(12) United States Patent
Elsheikh et al.

(10) Patent No.: US 8,076,521 B2
(45) Date of Patent: Dec. 13, 2011

(54) PROCESS FOR THE MANUFACTURE OF HYDROFLUOROOLEFINS

(75) Inventors: Maher Y. Elsheikh, Wayne, PA (US); Philippe Bonnet, Lower Merion, PA (US); Benjamin Bin Chen, Wayne, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 12/664,205

(22) PCT Filed: Jun. 26, 2008

(86) PCT No.: PCT/US2008/068293
§ 371 (c)(1),
(2), (4) Date: Dec. 11, 2009

(87) PCT Pub. No.: WO2009/003084
PCT Pub. Date: Dec. 31, 2008

(65) Prior Publication Data
US 2010/0185030 A1  Jul. 22, 2010

Related U.S. Application Data

(60) Provisional application No. 60/946,406, filed on Jun. 27, 2007.

(51) Int. Cl.
*C07C 17/20* (2006.01)
(52) U.S. Cl. .......... 570/160; 570/123; 570/153
(58) Field of Classification Search .......... None
See application file for complete search history.

(56) References Cited

U.S. PATENT DOCUMENTS

| | | | |
|---|---|---|---|
| 5,616,819 A * | 4/1997 | Boyce et al. .......... | 570/167 |
| 5,731,481 A | 3/1998 | Cherminal et al. | |
| 5,895,825 A * | 4/1999 | Elsheikh et al. .......... | 570/167 |
| 2007/0299286 A1 | 12/2007 | Elsheikh et al. | |

* cited by examiner

*Primary Examiner* — Sudhakar Katakam
(74) *Attorney, Agent, or Firm* — Steven D. Boyd

(57) ABSTRACT

In this invention we are disclosing a process for the synthesis of hydrochlorofluoro olefins (HCFO) and/or hydrofluoroolefins (HFO). The process is based on the following steps of liquid phase, noncatalytic fluorination of hydrochloropropenes to form hydrochlorofluoropropenes and/or hydrofluoropropenes, followed by gas phase, catalytic fluorination of the hydrochlorofluoropropenes to form hydrofluoropropenes.

20 Claims, No Drawings

PROCESS FOR THE MANUFACTURE OF HYDROFLUOROOLEFINS

FIELD OF THE INVENTION

The present invention relates to a process for the manufacture of a hydrofluoropropenes. More particularly, the present invention relates to a process for manufacturing the hydrofluoropropenes such as 1,1,1,2-tetrafluoropropene ("HFO-1234yf") from a chloropropene material such as 1,1,2,3-tetrachloropropene ("HCO-1230xa"). The process comprises two reactions, the first being a liquid phase, noncatalytic fluorination of the hydrochloropropene to form a hydrochlorofluoropropene (HCFO) and the second a catalyzed gas phase fluorination of the hydrochlorofluoropropene to form a hydrofluoropropene.

BACKGROUND OF THE INVENTION

The Montreal Protocol for the protection of the ozone layer, signed in October 1987, mandate the phase out of the use of chlorofluorocarbons (CFCs). Materials more "friendly" to the ozone layer, such as hydrofluorocarbons (HFCs) eg HFC-134a replaced chlorofluorocarbons. The latter compounds have proven to be green house gases, causing global warming and were regulated by the Kyoto Protocol on Climate Change. The emerging replacement materials, hydrofluoropropenes, were shown to be environmentally acceptable i.e. has zero ozone depletion potential (ODP) and acceptable low GWP. This present invention describes process for manufacturing of hydrofluoroolefins such as hydrofluoropropenes and/or hydrochlorofluoroolefins. The process of the present invention is based on a multi reaction process including a liquid phase, noncatalytic fluorination and a catalytic gas phase fluorination to produce desirable fluoroolefins.

Methods of preparing hydrofluoroalkenes are known. For example, WO2007/079431 discloses processes for the production of fluorinated olefins, including hydrofluoropropenes. The processes which are broadly described as a single reaction or two or more reactions involve fluorination of compound of the formula $C(X)_m CCl(Y)_n C(X)_m$ to at least one compound of formula $CF_3 CF=CHZ$, where each X, Y and Z is independently H, F, Cl, I or Br and each m is independently 1, 2 or 3 and n is 0 or 1. The examples and preferred embodiments are disclose multi-step process such a reaction sequence wherein a feedstock of 1,1,2,3 tetrachloropropene (1230xa) is fluorinated in a catalyzed, gas phase reaction to form a compound such as 2-chloro-3,3,3-tri-fluoropropene (1233xf). The 2-chloro 3,3,3-tri-fluoropropene is then converted to 2-chloro-2,3,3,3-tetrafluoropropane (244bb) via a liquid phase, catalyzed reaction. The 2-chloro-2,3,3,3-tetrafluoropropane is than dehydrochlorinated to 2,3,3,3-tetrafluoropropene (1234yf) via a catalyzed, gas phase reaction.

DESCRIPTION OF THE INVENTION

The present invention provides a process for producing a hydrofluoropropene of the formula $C_3H_{(a+x-1)}F_{7-(a+x)}$ where a=0, 1, 2, 3 or 4, x=0, 1, 2 or 3 and a+x is greater than or equal to 1, from "feedstock" of a tetrachloropropene comprising the steps of a) liquid phase, noncatalytic fluorination of the tetrachloropropene to form hydrochlorofluoropropene of the formula $C_3F_3H_{(a+x-1)}Cl_{4-(a+x)}$ and thereafter b) gas phase, catalytic fluorination of the hydrochlorofluoropropene to form a hydrofluoropropene of the formula $C_3H_{(a+x-1)}F_{7-(a+x)}$ preferably 2,3,3,3-tetrafluoropropene.

The first step of the present invention relates to liquid phase, uncatalyzed fluorination of a hydrochloropropene to form a hydrochlorofluoropropene of the formula $C_3F_3H_{(a+x-1)}Cl_{4-(a+x)}$. The uncatalyzed liquid phase process comprises contacting a hydrochloropropene of the formula $C_3H_{(a+x-1)}Cl_{7-(a+x)}$ with HF. The HF to hydrochloropropene molar ratio is from at least about 3 to 1 to about 500 to 1, preferably from about 10 to 1 to about 200 to 1. The reaction temperatures can vary from about 20° C. to about 300° C., preferably from about 50° C. to about 150° C. Operating pressures can range from about 100 to about 900 psig, preferably from about 250 to about 700 psig. Residence time is normally from about ¼ to 24 hours, preferably from about ½ hour to about 2 hours. Any unreacted feedstock can be easily separated from the desired product due to the large difference in their boiling points. The reaction produces the desired hydrochlorofluoropropene which is essentially oligomer free. The reaction vessel is preferably constructed from material resistant to HF, known in the art such 316L stainless steel, Inconel or Hastelloy. The reaction can be carried out via a continuous or batch process. The principal by-product of this reaction is hydrogen chloride (HCl), which may be removed by conventional means known in the art (such as absorption or distillation). After removal of HCl, the product stream contains the desired hydrochlorofluoropropene product, such as HCFC-1233xf, and may include co-products and unreacted starting materials including but not limited to: HF, pentafluoropropane such as 245cb and chlorotetrafluoropropane such as 244bb. This stream provides the feedstock for the final reaction step.

The final reaction step of the present invention relates a gas phase, catalytic fluorination of the hydrochlorofluoropropene from the first reaction step, to form a hydrofluoropropene of the formula $C_3H_{(a+x-1)}F_{7-(a+x)}$. The process involves contacting the hydrochlorofluoropropene with HF in a first reaction zone under conditions sufficient to produce a three carbon hydrofluoroolefin of the formula $C_3H_{(a+x-1)}F_{7-(a+x)}$. The HF:hydrochlorofluoroolefin molar ratio is typically from about 0.5:1 to 40:1, but is preferably at least about 1:1 to enhance conversion and preferably no more than about 10:1 in order to produce lower levels of HF which are recovered downstream. Temperatures of from about 250° C. to about 600° C. are typically used, preferably from about 300° C. to about 500° C. Pressures are typically from about atmospheric to about 400 psig, preferably from about 50 to 200 psig. Co-products formed such as 245cb and/or 244bb can be recycled back to the gas phase reactor.

A variety of fluorination catalysts can be used, such as aluminum fluoride or a chromium-based catalyst (such as chromium oxide, $Cr_2O_3$), which chromium-based catalyst is either unsupported or supported. The support is selected from fluorided alumina, activated carbon and the like. The chromium catalyst being used alone or in the presence of a co-catalyst such as zinc, manganese, cobalt or nickel. Three such preferred chromium catalysts are pure chromium oxide, chromium/nickel with nickel co-catalyst and chromium/nickel supported on fluorinated alumina. Preparation of this latter catalyst being disclosed, for example, in U.S. Pat. No. 5,731,481. The chromium-based catalysts are preferably activated before use, typically by a procedure wherein the catalyst bed is heated to about 370°-380° C. (normally with a continuous flow of nitrogen), after which a mixture of approximately equal volumes of HF and air or nitrogen (preferably nitrogen)

are fed over the catalyst bed for about 18 hours at higher pressure, varied between 100-200 psig. US 2007/0299286 sets out a suitable catalyst activation process.

An oxygen, oxygen containing compound, chlorine, or other oxidizer can be used as a co-feed to extend the catalyst lifetime, typically in an amount of from about 0.005 to about 1 mole % of chlorine or oxygen per mole of organic in the feed. The oxygen being introduced as an oxygen-containing gas such as air, oxygen, or an oxygen/nitrogen mixture. Contact times (catalyst volume divided by the total flow rate of reactants and cofeeds at the operating temperature and pressure of the process) are preferably from about 1 to about 250 seconds, more preferably from about 1 to about 50 seconds.

The reaction product of the gas phase, catalytic fluorination step will include, in addition to the desired hydrofluoropropene, unreacted hydrochlorofluoropropene, and fluro- and chlorofluor-substituted propane such as 245cb and 244bb. These byproducts can be separated from the desired hydrofluoropropene in a series of two or more separation columns with the by products being recycled to the gas phase, catalytic fluorination reaction.

The tetrachloropropene feedstock of the present invention can be formed via variety of ways as would be know by a person skilled in the art.

EXAMPLES

The data presented in the examples was calculated based upon results obtained in comparable reactions with closely related materials.

Example 1

Uncatalyzed Liquid Phase Fluorination of 1,1,2,3 tetrachloropropene (HCO-1230xa) to 2-chloro-3,3,3-trifluoropropene (HCFO-1233xf)

0.28 moles of HCO-1230xa can be loaded into a 300 ml Hastelloy C autoclave equipped with gas inlet valve, mechanical stirrer and an outlet cooling tower. 3.5 moles of HF gas can be condensed in the autoclave. The reaction mixture would be gradually heated up to 120° C., with continuous stirring for approximately ½ hour. Excessive gas pressure resulted from the formation of HCl can be vented through a 400 psi pressure relief valve on the cooling tower. The high boiling material would be trapped at room temperature. The volatile organic products could be dried over anhydrous calcium sulfate and collected in a cold trap. Nearly 0.28 moles of the 2-chloro-3,3,3-trifluoropropene product, would be found in the cold trap. Examples 1, 2 and 3, summarized in Table 1, were calculated based upon comparable reactions with closely related materials.

TABLE 1

Summary of the results, uncatalyzed liquid phase fluorination of 1230xa to 1233xf

| Example | 1 |
|---|---|
| Temperature ° C. | 100 |
| Pressure psig | 300 |
| Mole Ratio HF/1230za | 166 |
| Residence time, hours | 5 |
| % Conversion 1230xa | 100 |
| % 1234yf | 0.25 |
| % 245cb | 0.16 |

TABLE 1-continued

Summary of the results, uncatalyzed liquid phase fluorination of 1230xa to 1233xf

| Example | 1 |
|---|---|
| % 1233xf | 97.2 |
| Other | 2.39 |

1234yf is $CF_3CF=CH_2$
245cb is $CF_3CF_2CH_3$
1233xf is $CF_3CCl=CH_2$
244bb is $CF_3CFClCH_3$

Examples 2-4

Gas Phase Fluorination of HCO-1233xf at High Temperature

An activated catalyst, 15 cc, could be loaded into a vertical fix bed reactor (20 inches by 1 inch Hastelloy C). HF could be fed as a liquid, and converted to a gas using vaporizer. HCO-1233xf could be fed to the fix bed reactor using a syringe pump and heated up to 365° C. The reaction would be run at a pressure of between 42-162 psi. Table 3 summarizes the calculations of expected results using a variety of molar ratio of HCO-1233xf/HF and contact times based upon comparable reactions with closely related materials.

TABLE 3

Summary of fluorinating 1233xf to 1234yf, using unsupported 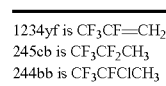 catalyst

| Example | 2 | 3 | 4 |
|---|---|---|---|
| Temp ° C. | 365 | 365 | 365 |
| Pressure psig | 48.5 | 48.5 | 169 |
| $O_2$/1233xf ratio | 0.5 | 0.5 | 0.5 |
| HF/1233xa Molar Ratio | 10.6 | 21.1 | 21.1 |
| Contact Time sec. | 3.9 | 4 | 14 |
| % Conversion | 54.8 | 64.1 | 73.6 |
| % 1234yf | 58.3 | 56.4 | 40.6 |
| % 245cb | 36.6 | 36.5 | 59.4 |
| % 244bb | 5.1 | 7.1 | 0 |

1234yf is $CF_3CF=CH_2$
245cb is $CF_3CF_2CH_3$
244bb is $CF_3CFClCH_3$

While the present invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

The invention claimed is:

1. A process for producing 1,1,1,2-tetrafluoropropene, comprising the steps of:
   a) fluorinating 1,1,2,3-tetrachloropropene, in a liquid phase, without catalyst, to form 2-chloro-3,3,3-tri-fluoropropene and HCL and first co-products; and thereafter
   b) fluorinating said 2-chloro-3,3,3-tri-fluoropropene, in a gas phase, in the presence of a catalyst selected from the group consisting of aluminum fluoride, supported chromium catalyst, unsupported chromium catalyst and mixtures thereof, to form 1,1,1,2-tetrafluoropropene and second co-products.

2. The process of claim 1 wherein the step a) of fluorinating said 1,1,2,3-tetrachloropropene in a liquid phase, without catalyst comprises contacting said 1,1,2,3-tetrachloropropene with hydrogen fluoride.

3. The process of claim 1 further comprising the step of separating HCl from said 2-chloro-3,3,3-tri-fluoropropene and HCL and first co-products prior to fluorinating said 2-chloro-3,3,3-tri-fluoropropene.

4. The process of claim 1 wherein said first co-products comprise pentafluoropropane and chlorotetrafluoropropane.

5. The process of claim 4 wherein said pentafluoropropane comprises HFC-245cb and said chlorotetrafluoropropane comprises HCFC-244bb.

6. The process of claim 1 further comprising the step of separating said second co-products from said 1,1,1,2-tetrafluoropropene.

7. The process of claim 6 further comprising the step of recycling said separated second co-products to step a).

8. The process of claim 1 wherein said second co-products comprise pentafluoropropane and chlorotetrafluoropropane.

9. The process of claim 8 wherein said pentafluoropropane comprises HFC-245cb and said chlorotetrafluoropropane comprises HCFC-244bb.

10. The process of claim 2 wherein the ratio of 1,1,2,3-tetrachloropropene to hydrogen fluoride ranges from about 3 to 1 to about 500 to 1.

11. The process of claim 2 wherein the ratio of 1,1,2,3-tetrachloropropene to hydrogen fluoride ranges from about 10 to 1 to about 200 to 1.

12. The process of claim 2 wherein the temperature ranges from about 20° to about 300° C.

13. The process of claim 2 wherein the temperature ranges from about 50° to about 150° C.

14. The process of claim 2 wherein the pressure ranges from about 100 to 900 psig.

15. The process of claim 2 wherein the pressure ranges from about 250 to 700 psig.

16. The process of claim 1 wherein the step of fluorinating the 2-chloro-3,3,3-tri-fluoropropene in a gas phase, in the presence of said catalyst comprises contacting said 2-chloro-3,3,3-tri-fluoropropene with hydrogen fluoride in the presence of said catalyst.

17. The process of claim 16 wherein said process further comprises a co-catalyst.

18. The process of claim 17 wherein said co-catalyst is selected from the group consisting of nickel, zinc, cobalt and manganese.

19. The process of claim 1 wherein said catalyst is activated prior to use.

20. The process of claim 19 wherein said catalyst is activated at a pressure above about 150 psi prior to use.

* * * * *